(12) United States Patent
Feriani et al.

(10) Patent No.: US 7,694,892 B2
(45) Date of Patent: Apr. 13, 2010

(54) LIQUID DROPLET PLUG AND SPRAY SYSTEM

(75) Inventors: Amir Feriani, Auvernier (CH); Joseph Hess, Bevaix (CH); Philippe Luginbuhl, Nods (CH); Raphael Weber, La Chaux-de-Fonds (CH); Jacques Blanie, Unna (DE); Reiker Canfield, Crystal Lake, IL (US)

(73) Assignee: EP Systems SA, Neuchâtel (CH)

( * ) Notice: Subject to any disclaimer, the term of this patent is extended or adjusted under 35 U.S.C. 154(b) by 901 days.

(21) Appl. No.: 11/037,473

(22) Filed: Jan. 19, 2005

(65) Prior Publication Data

US 2005/0230495 A1 Oct. 20, 2005

(30) Foreign Application Priority Data

Jan. 26, 2004 (EP) .................................. 04001566

(51) Int. Cl.
 *B05B 1/08* (2006.01)
(52) U.S. Cl. ........................................ 239/102.2; 239/86
(58) Field of Classification Search .................. 239/86, 239/102.1, 102.2
 See application file for complete search history.

(56) References Cited

U.S. PATENT DOCUMENTS

| 5,404,871 | A | 4/1995 | Goodman et al. |
| 5,487,378 | A | 1/1996 | Robertson et al. |
| 5,518,179 | A | 5/1996 | Humberstone et al. |
| 5,749,519 | A | 5/1998 | Miller |
| 6,062,212 | A | 5/2000 | Davison et al. |
| 6,196,219 | B1 * | 3/2001 | Hess et al. ............. 128/200.21 |
| 6,540,153 | B1 | 4/2003 | Ivri |
| 2002/0070239 | A1 | 6/2002 | Garcia et al. |
| 2002/0185125 | A1 | 12/2002 | Klimowicz et al. |

FOREIGN PATENT DOCUMENTS

| EP | 1 005 916 A1 | 6/2000 |
| EP | 0 923 957 B1 | 10/2001 |

OTHER PUBLICATIONS

European Search Report, completed May 25, 2004.

* cited by examiner

*Primary Examiner*—Christopher S Kim
(74) *Attorney, Agent, or Firm*—Griffin & Szipl, P.C.

(57) ABSTRACT

The invention concerns a Liquid droplet plug & spray system for atomising a liquid substance and comprising a liquid droplet spray device including a housing in which a space is provided for receiving a liquid substance, a reservoir for containing said liquid substance, a fluidic interface for connecting said reservoir to said space in said housing thereby conveying liquid substance contained in said reservoir to said space by way of capillary action, a valve arranged between said reservoir and said fluidic channel for controlling access of said liquid substance from said reservoir to said fluid channel, an electromechanical actuation means for actuating the liquid substance in said space such that the liquid substance undergoes a vibration and is expelled as a liquid droplet spray, and electronic control means for controlling said electromechanical actuation means, wherein said liquid droplet spray system consists of two parts, a first, disposable part in which said reservoir and said valve are arranged, and a second, non-disposable part in which said liquid droplet spray device, said electromechanical actuation means, said electronic control means and said liquid channel are arranged such that said reservoir does not directly contact said liquid channel, said valve ensuring that said first, disposable part is liquid tight when not in use.

20 Claims, 3 Drawing Sheets

LIQUID DROPLET PLUG AND SPRAY SYSTEM

Figure 1:
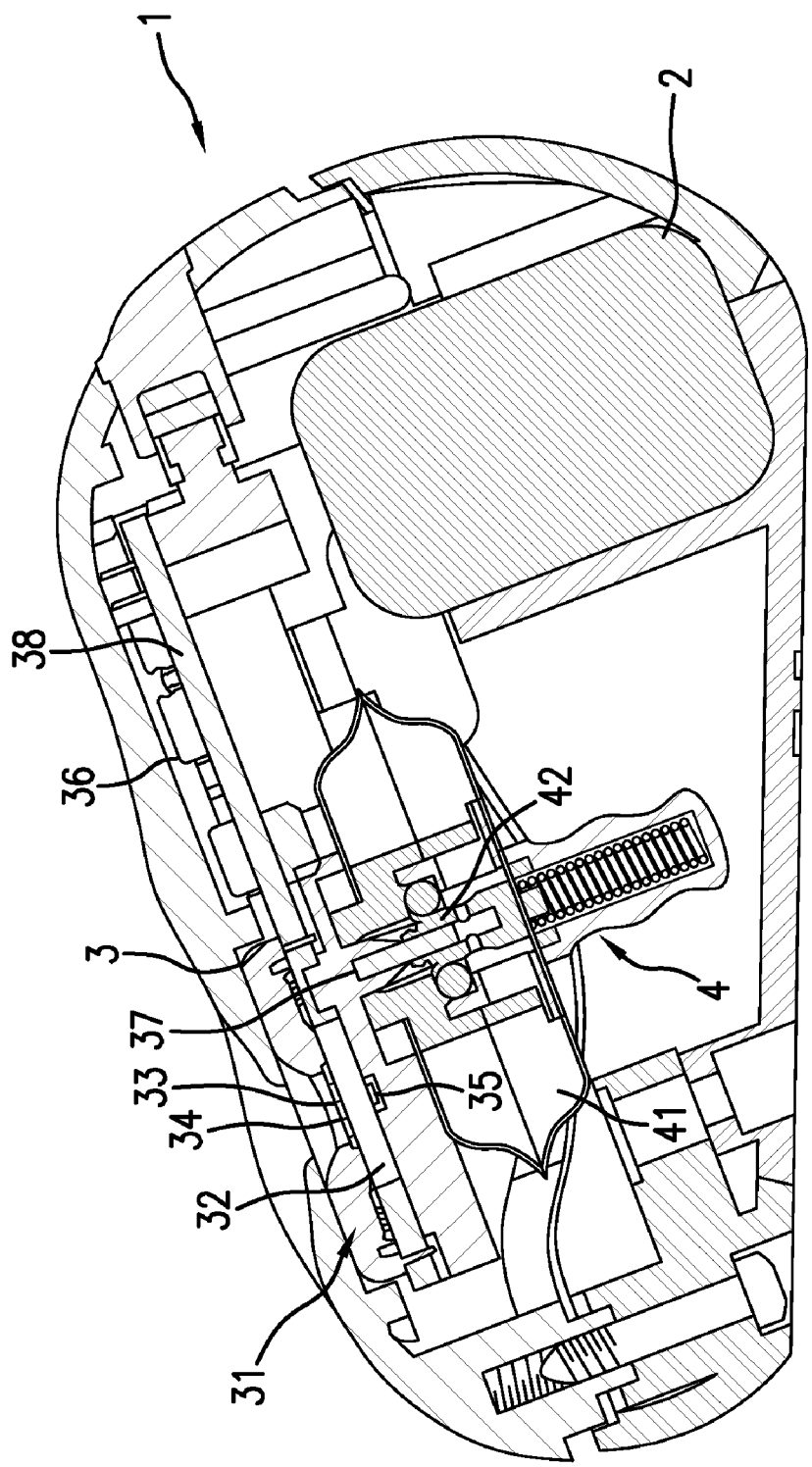

This application claims priority from European Patent Application No. 04001566.1, filed Jan. 26, 2004, the entire disclosure of which is incorporated herein by reference.

The present invention relates to a liquid droplet plug & spray system comprising a liquid droplet spray device suitable for atomising a liquid substance, such as a personal or an ambient fragrance or a functional liquid such as an insecticide or a medicated liquid. Such a device may be used, e.g., for fragrance or functional or medical liquid dispensers, for an inhaler or the like, for controlled release of droplets of such. More specifically, the present invention concerns a liquid droplet spray system which is of modular design having a disposable part and a permanent, non-disposable part.

Various devices are known for atomising a liquid. For example, the documents EP 0923957 and EP 1005916, both in the name of the present Applicant describe a liquid droplet spray device. A brief description of the liquid droplet spray device known from these documents, which are hereby incorporated by reference, is given here.

The spray device of the above-referenced documents consists of a housing formed of a superposition of a first substrate and a second substrate in-between which a space is formed for containing a liquid substance. One of the substrates contains outlet means containing outlet nozzles and output channels connecting these nozzles to the space.

A liquid substance enters the spray device by way of, e.g., a very low pressure, e.g., around a few millibar or slightly negative pressure, or capillary action. This can be achieved for example by way of at least one input tube or needle through which the liquid substance may be supplied from an external reservoir into the spray device. The spray device further comprises a vibrating element, e.g. a piezoelectric element to cause vibration of the liquid substance in the space so as to cause the liquid to be ejected as a spray of droplets. There is no description of a system or of the arrangement of the external reservoir with respect to the device.

A liquid droplet spray system is known from the document U.S. Pat. No. 5,749,519. This device relates to an air freshener which has a reservoir for containing an air freshener liquid. The reservoir is connected to a vapour-emanating surface of a liquid dispensing device by way of a wick. The liquid is transmitted from the reservoir via the wick through capillary action to the vapour-emanating surface so as to dispense the air freshener.

Due to its design, and in particular due to the use of a wick, the liquid dispensing device always transmits the liquid to the vapour-emanating surface. Thus, to avoid waste and spill, the device is provided in a housing having a cover for sealing the vapour-emanating surface. Once the cover is removed, the vapour is dispensed into the surrounding air.

However, when the reservoir needs to be exchanged, the user will receive air freshener on his hands when manipulating the reservoir due to the wick being in contact with the liquid. Of course, air fresheners are of nature of strong fragrance so that this is not very pleasant. Further, this leads to a loss of liquid if one forgets to put the cover back on, and it is impossible to allow for a controlled dispersion of the vapour amount.

Another liquid droplet spray system is known from the document US 2002/0070239. This system has a reservoir, a flexible pouch, containing a porous material for absorbing the liquid of the reservoir. The reservoir is connected to a capillary channel, also containing a porous material, such as a wick. The channel leads the liquid to a perforated membrane surface. When the surface is vibrated by further provided vibration means, the liquid is dispensed as droplets.

Here again, a wick is used, both in the reservoir and in the capillary channel. Thus, when changing the reservoir, it would appear impossible to do such without any liquid spilling out.

Further, due to the design of the system, liquid may leak through the perforated membrane even when the system is not in use thus leading to wastage and related inconveniences such as unwanted fragrancing. Of course, controlled dispensing is not possible either with this system.

Another droplet spray device is known from the document U.S. Pat. No. 6,062,212 which describes a liquid dispenser having vibration means which are activated to expel liquid from a mesh in the usual manner, but which remain activated to ensure a complete emptying of the liquid from the dispenser. The disadvantage is that this additional atomising duration will sometimes be either too long or too short and that a fixed time will not work with liquids of various viscosities and surface tensions and ambient conditions.

It is, therefore, an object of the present invention to provide a liquid droplet spray system that overcomes the above-mentioned inconveniences and that can be efficiently used for liquid substances such as perfumes or other non-aqueous solvent based liquids, or for liquid medicaments.

It is another object of the present invention to provide such a system that is simple, reliable and inexpensive to manufacture, small in size and low in energy consumption and cost, and as such suitable as a personal or ambient fragrance and functional liquid dispenser.

Thus, the present invention concerns a liquid droplet spray system as defined in the appended claims.

Thanks to the construction of the liquid droplet spray system according to the present invention an efficient system may be obtained in a relatively simple and inexpensive manner.

Furthermore, due to the modular design of the system, it is possible to easily exchange the reservoir without any unwanted spill or wastage of liquid contained in the reservoir. In fact, the system comprises a disposable part and a permanent, non-disposable part, wherein the disposable part comprises the reservoir containing the liquid substance as well as a valve ensuring that the disposable part is liquid tight even when removed from the system.

Figure 2A:
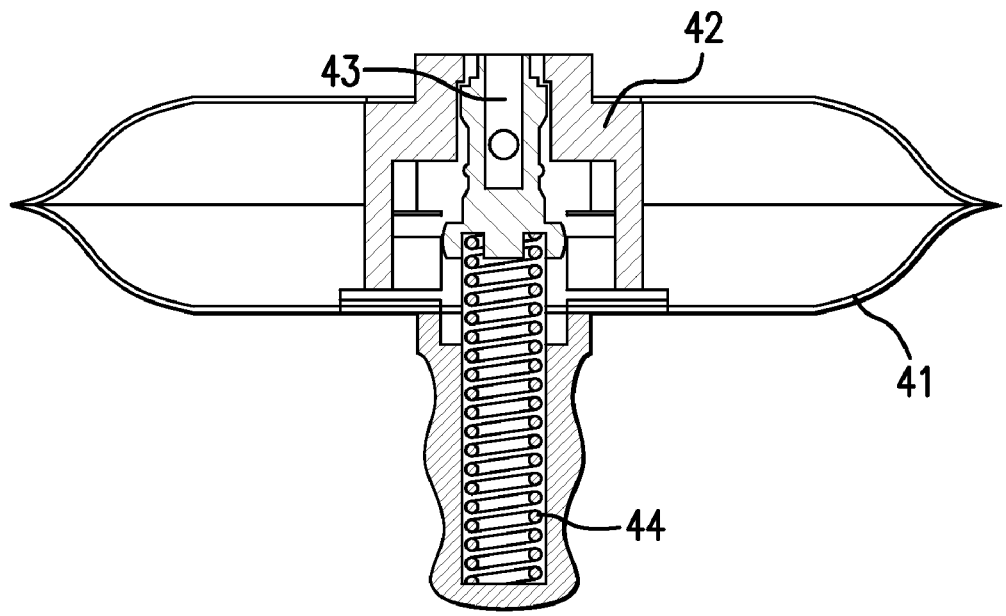
Figure 2B:
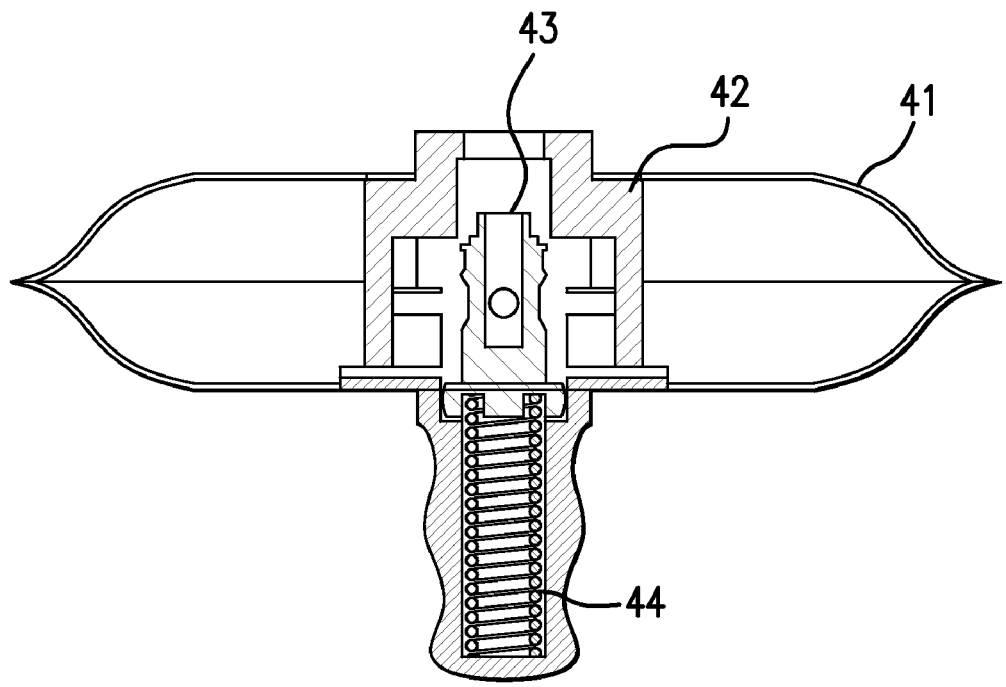

Other features and advantages of the liquid droplet spray system according to the present invention will become clear from reading the following description, which is given solely by way of a non-limitative example thereby referring to the attached drawings in which:

FIG. 1 is a schematic cross-section of a liquid droplet spray system according to the present invention, FIGS. 2a and 2b show schematic detailed views of an example of the disposable part of the liquid droplet spray system of FIG. 1, and FIGS. 3a to 3f show stepwise the connection of a capillary liquid channel to a valve and reservoir of a disposable part of the liquid droplet plug and spray system according to the present invention.

An example of a preferred embodiment will be described hereafter.

FIG. 1 shows a liquid droplet plug and spray system indicated by general reference 1. This system contains a power source such as a battery 2, a permanent, non-disposable part 3, and a disposable part 4. Permanent part 3 comprises a liquid droplet spray device whose housing 31 encloses a space 32.

Advantageously, this spray device may be similar to that as described in the above-referenced documents EP-A-0 923

957 and EP-A-1 005 916, both in the name of the present Applicant, but other spray devices, or atomisers, may be used instead. Space 32 constitutes a liquid substance chamber, for example for containing ambient or personal fragrance or some other liquid, directly or entrapped, partially or totally, in a soft porous medium. A perforated membrane 33 having one or more perforations 34 is provided to cover space 32 and through which perforations 34 liquid contained in space 32 may be expelled as a spray of fine droplets. To this effect, an electromechanical actuator 35 such as a piezoelectric element is provided on housing 31 and arranged to act on a liquid substance contained in space 32 such that this liquid substance undergoes a vibration and contacts the perforated membrane 33 causing the liquid substance to traverse the perforations 34 and be expelled as a liquid droplet spray.

Permanent part 3 further comprises an electronic means 36, such as an ASIC, for controlling the electromechanical actuator 35.

Further, appropriate fluidic interface means, such as, in its simplest form, a capillary channel 37 is connected to housing 31 for supplying the liquid substance to and allowing exiting from space 32. Such fluidic interface may further comprise for example a measurement means such as a sensor or connection means as may be understood from the following.

This fluidic interface, or capillary channel 37 can also contain a soft porous medium, connected on one side to space 32, and connectable on another side to disposable part 4 as will be described in more detail further on. Disposable part 4 thus comprises a reservoir 41 such as a sealed polymer bag or other known reservoir for liquids, and a valve 42 arranged to connect reservoir 41 with capillary channel 37. This valve 42 is arranged such that it ensures that disposable part 4 is liquid tight when removed from the system.

As can be understood from the above, there is no direct connection between the fluidic interface 37 and reservoir 41, but only between the fluidic interface and valve 42, on the one hand, and valve 42 and reservoir 41, on the other hand.

Thanks to this arrangement, it is possible to readily remove disposable part 4 from the system, for example when the reservoir is empty or when exchanging a reservoir containing one liquid substance against one with a different liquid substance is required without any leakage of liquid from disposable part 4 or from non-disposable part 3.

FIGS. 2a and 2b show in more detail the elements of disposable part 4. FIG. 2a shows reservoir 41 connected to valve 42 which is in a closed position so that disposable part 4 is liquid tight, and FIG. 2b shows the valve in an open position so that liquid may exit reservoir 41 and thus the disposable part. Valve 42 may be any well-known valve as long as it can be positioned from one position to another, thereby blocking or releasing the liquid substance.

In this embodiment, valve 42 comprises a piston 43 that is operated by a spring 44 so as to move the piston from an upper position, in which the valve is closed, see FIG. 2a, to a lower position in which the valve is open, see FIG. 2b. Other means besides a spring are of course also possible to actuate the piston. Advantageously, a hydrodynamic valve as described in co-pending application EP 03019452.6 in the name of the present Applicant may be used. Of course, an electromechanical valve may also be used.

FIG. 3 shows stepwise the connection of capillary liquid channel 37, forming part of permanent non-disposable part 3, to valve 42, forming part of disposable part 4. In FIG. 3a, valve 42 is in its closed position, with piston 43 in the upper position. Capillary channel 37 has a needle shape in this example and is positioned above the valve to allow for alignment with an insertion hole provided in valve 42 for receiving the capillary channel. In FIG. 3b, capillary channel 37 is inserted into valve 42 which still remains in the closed, upper, position. Thus, there is still no liquid connection between the disposable part and the permanent part. Next, in FIG. 3c, the valve is activated by moving piston 43 to its lower position thus establishing a liquid connection between the disposable part and permanent part.

At this stage, liquid contained in reservoir 41 enters the valve and then seeps into capillary channel 37 after which it reaches space 32 of the liquid droplet spray device in permanent non-disposable part 3. Thus, here the plug and spray system is ready for operation. As soon as electromechanical actuator 35 is activated, liquid contained in space 32 is expelled as a spray of fine droplets.

Figure 3C:
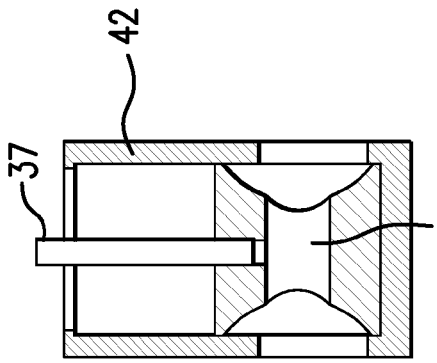
Figure 3F:
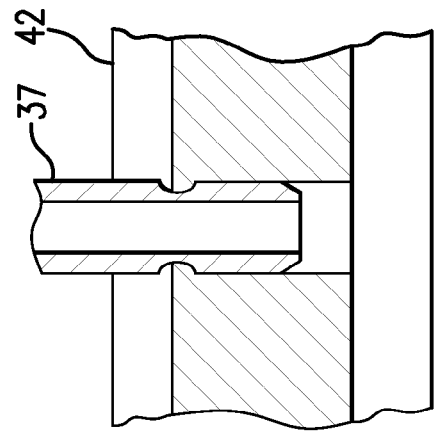
Figure 3B:
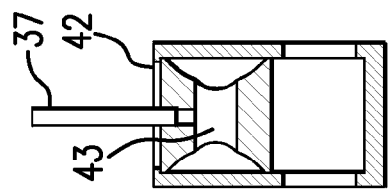
Figure 3E:
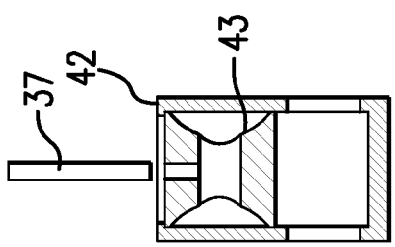
Figure 3A:
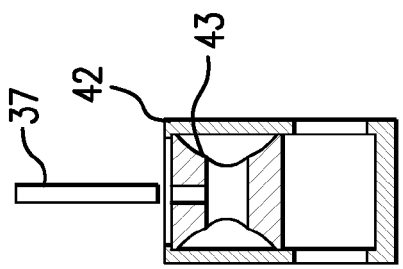
Figure 3D:
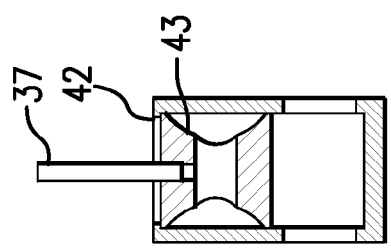

When it is necessary to remove reservoir 41, either when its contents is empty or if a different liquid is to be used in the system, the lower part of the disposable part 4 may be pulled, so that piston 43 will move back into its higher position due to the force applied to it by capillary channel 37 still in contact therewith thus closing the valve and ensuring that disposable part 4 is liquid tight, see FIG. 3d.

Next, as shown in FIG. 3e, disposable part 4 is disconnected from capillary channel 37 thus allowing for removal and replacement of the disposable part while valve 42 remains closed. No liquid will leak during this operation.

FIG. 3f, finally, shows a possible way of ensuring a correct connection between capillary channel 37 and valve 42. Thus, a simple click and fit connection may be used. Of course, it is also possible to use a conical connector, or any other well-known connector which ensures a leak tight connection.

As can be understood from the above, when the disposable part 4 is not in use, or is not connected to the permanent, non-disposable part 3 of the present liquid droplet plug and spray system, the valve ensures that the disposable part is liquid tight. When the disposable part is connected to the permanent part, the liquid substance enters the capillary channel, and reaches space 32. Due to the use of the space in combination with an actuation means, the liquid will remain in space 32, and only exit there from once the actuation means starts vibrating. Thus, space 32 constitutes a capillary filling and holding chamber as well as a pressure chamber for receiving the liquid substance, in a manner as explained in the above referenced documents EP 0923957 and EP 1005916.

Thanks to the above structure, once valve 42 is opened, liquid from reservoir 41 will flow automatically as the liquid substance will first enter valve 42, and then enter capillary channel 37 and space 32. Depending on the viscosity of the liquid substance, it may be useful to add a soft porous member in the channel, or also in space 32 to facilitate conveying of the liquid to space 32.

Advantageously, such soft porous medium may extend beyond the liquid capillary channel 37 into space 32 of the housing, or even extend until the inner periphery of the space, or even still fill space 32.

As mentioned above, electronic control means 36 are provided in non-disposable part 3 to activate the actuation means 35. To this effect, a support 38, see FIG. 1, may be provided for receiving the electronic means and/or electromechanical actuator 35. Support 38 may be formed integrally with capillary channel 37 to form the fluidic interface.

Advantageously, support 38 may be a flexible electric circuit board or a PCB.

In certain circumstances, some liquid might remain in space 32 after excitation by the electromechanical actuator 35. This could be the case if a larger volume had been pre-dosed than would actually be used. This could be an advantage for example in the dispensing of fine fragrances, where one would want to provide a continuous spray of a fine dry type of perfume spray action instead of the repeated pumping action required by current perfume pumps. However the pre-dosed volume might sometimes be too large and should thus not be expelled fully. In these cases support 38 and valve 42 will comprise means (not shown) to re-direct the excess liquid back into reservoir 41, either in the main reservoir itself, or in a separated container provided to this effect. In certain cases, it may also be necessary to avoid contamination of space 32 with a possibly different liquid substance, thus to ensure an empty space 32. To this effect, reservoir 41 may further comprise a buffer zone which is normally empty and is arranged to receive excess liquid substance that is not ejected from said space. This buffer zone could be a part of the main reservoir, or a separated section in liquid contact there with. The reservoir itself may be a form, fill and seal reservoir, such as a simple bag, or it may be of the airless type, or even of the solid type.

Further, the reservoir may be provided with electronic storing means such as a layer consisting of resistors and/or capacitors elements laminated into the reservoir material. The exact configuration of the resistors and/or capacitors elements can thus provide information about the content of the reservoir. For example, a certain resistance or capacitance may be indicative of a certain liquid substance, of the level, such as empty or not, of the liquid substance in reservoir 41, or even of the required use of the liquid substance. For example, if the liquid substance is a medicament, the information could be related not only to the identification of the liquid substance, but also to its use, such as the dosage that should be expelled, the frequency thereof, its expiation date etc. Another way of providing this information is by using a radiofrequency identification tag (RF ID tag).

Advantageously, the storing means may also uniquely identify the reservoir thus inhibiting the use of non-conformal reservoirs with the liquid droplet plug and spray system.

By linking this information to electronic means 36 provided in the permanent, non-disposable part 3, it is possible to control the use of reservoir 41. Thus, the electronic control means may then control the ejecting of liquid from the spray device, not only by controlling the electromechanical actuation means 35, but further also by processing the information from the reservoir.

Advantageously, an electronic valve control means of valve 42 may be provided to control the release of liquid substance from reservoir 41 in accordance with the information processed.

As may be understood, the electronic control means 36 of permanent part 3 may also be further provided with input means for external control signals. As such, it is possible to control the release of the liquid substance from the system as a function of externally applied signals. For example, the liquid droplet plug and spray device could be arranged to fit into an extension slot module of a video game playing station so as to allow for triggering of fragrances from the liquid droplet plug and spray system by the video game device which may provide signals to electronic means 36.

Further, liquid channel 37 may further comprise measurement means, not shown, arranged, in a suitable manner, to measure, directly or indirectly, the flow of the liquid substance through channel 37. Such measurement means are known as such, and thus are not further described here. Preferably, such measurement could be linked to electronic control means 36 or to the valve control means to allow for opening or closing of the valve as a function of the measured flow. Indeed, since all internal volumes, flow rates and their proportion relative to the total volume are known, such measurement means can be calibrated precisely in a volumetric manner to stop electromechanical actuation means 35 via electronic means 36 at the instance when space 32 is empty, thus avoiding operation of electromechanical actuation means 35 longer than necessary.

Thanks to the above described features of the present liquid droplet plug and spray system, it is possible to use the system for atomising a liquid substance, such as perfume or medicaments, so that the system can be used for example as a nebuliser, a perfume dispenser, an inhaler, a nasal spray, or an ophthalmologic dispenser, or the like with an easily exchangeable reservoir which does not dispense any liquid substance when not in use.

Having described a preferred embodiment of this invention, it will now be apparent to one of skill in the art that other embodiments incorporating its concept may be used. It is felt, therefore, that this invention should not be limited to the disclosed embodiment, but rather should be limited only by the scope of the appended claims.

The invention claimed is:

1. Liquid droplet spray system for atomising a liquid substance, the liquid droplet spray system comprising:
   a liquid droplet spray device including a housing in which a space is provided, said space being arranged to receive said liquid substance, the housing including a perforated membrane having one or more perforations and covering said space such that said liquid substance may exit the space and the device by traversing the one or more perforations of said perforated membrane,
   a reservoir for containing said liquid substance,
   a fluidic interface comprising a fluid channel arranged to connect said reservoir to said space in said housing thereby conveying liquid substance contained in said reservoir to said space by way of capillary action,
   a valve arranged between said reservoir and said fluidic interface comprising said fluid channel for controlling access of said liquid substance from said reservoir to said fluid channel,
   an electromechanical actuation means arranged to actuate liquid substance in said space such that the liquid substance undergoes a vibration and contacts the perforated membrane thereby traversing the one or more perforations as a liquid droplet spray, and
   electronic control means arranged to at least control said electromechanical actuation means,
   wherein said reservoir and said valve are arranged in a first, disposable part, and said liquid droplet spray device, said electromechanical actuation means, said electronic control means and said fluidic interface are arranged in a second, non-disposable part such that said reservoir does not directly contact said fluid channel, said valve ensuring that said first, disposable part is liquid tight when not in use.

2. Liquid droplet spray system according to claim 1, wherein said fluidic interface contains a soft porous medium capable of facilitating the conveying of said liquid substance.

3. Liquid droplet spray system according to claim 2, wherein said soft porous medium extends beyond the fluidic interface into said space of the housing.

4. Liquid droplet spray system according to claim 3, wherein said soft porous medium extends until the inner periphery of said space.

5. Liquid droplet spray system according to claim 4, wherein said soft porous medium fills said space.

6. Liquid droplet spray system according to claim 1, wherein said fluidic interface on said second, non-disposable part further comprises a support for receiving said electronic means and/or said electromechanical actuation means.

7. Liquid droplet spray system according to claim 6, wherein said support is a flexible electric circuit board.

8. Liquid droplet spray system according to claim 6, wherein said support is a PCB.

9. Liquid droplet spray system according to claim 1, wherein said reservoir further comprises a buffer zone which is normally empty and is arranged to receive excess liquid substance that is not ejected from said space.

10. Liquid droplet spray system according to claim 1, wherein said fluidic interface further comprises means to re-direct any excess liquid substance back to said reservoir.

11. Liquid droplet spray system according to claim 1, wherein said liquid channel further comprises measurement means arranged, in a suitable manner, to measure, directly or indirectly, the flow of said liquid substance through said channel.

12. Liquid droplet spray system according to claim 1, wherein said reservoir is a form, fill and seal type reservoir, an airless reservoir, or a solid reservoir.

13. Liquid droplet spray system according to claim 1, wherein at least a part of said reservoir is provided with, in a suitable manner, storing means arranged to store information about the identification of the contents of the reservoir and of the use of the contents.

14. Liquid droplet spray system according to claim 13, wherein said storing means stores information indicative of the level of the contents of said reservoir.

15. Liquid droplet spray system according to claim 13, wherein said storing means is a foil containing a layer of resistors and/or capacitors elements laminated into at least a part of the reservoir.

16. Liquid droplet spray system according to claim 1, wherein said electronic means further controls the release of said liquid substance from said liquid droplet spray device.

17. Liquid droplet spray system according to claim 1, further comprising valve control means for controlling the opening and closing of said valve.

18. Liquid droplet spray system according to claim 17, wherein said electronic means further controls the release of said liquid substance from said reservoir to said space by controlling said valve control means.

19. Liquid droplet spray system according to claim 18, wherein said electronic control means are responsive to external signals for triggering the release of said liquid substance.

20. Liquid droplet spray system according to claim 18, wherein said electronic control means are responsive to signals from said measurement means for triggering and stopping the release of said liquid substance.

* * * * *